United States Patent [19]

Khartchenko et al.

[11] Patent Number: 5,403,749
[45] Date of Patent: Apr. 4, 1995

[54] REAGENT FOR THE DETERMINATION OF ETHANOL AND METHOD OF DETERMINATION OF PRESENCE OF ETHANOL IN THE HUMAN BODY

[75] Inventors: Serguei V. Khartchenko, c/o 1405 Toronto Dominion Tower, Edmonton Centre, Edmonton, Alberta T5J 0Z2, Canada; Kiril Giatsintov, Mountainside, N.Y.; Andrei V. Aleksandrov, Moscow, U.S.S.R.; Nadejda P. Khartchenko, Edmonton, Canada

[73] Assignee: Serguei V. Khartchenko, Edmonton, Canada

[21] Appl. No.: 48,440

[22] Filed: Aug. 13, 1992
(Under 37 CFR 1.47)

[51] Int. Cl.⁶ .............................................. G01N 33/00
[52] U.S. Cl. .................................. 436/132; 436/169; 422/56; 422/57; 422/85
[58] Field of Search ............... 436/132, 169, 179, 180; 422/56, 85, 57

[56] References Cited

U.S. PATENT DOCUMENTS

| Re. 27,008 | 12/1970 | Luckey | 436/132 |
|---|---|---|---|
| 2,939,768 | 6/1960 | Grosskopf | 436/132 |
| 3,208,827 | 9/1965 | Borkenstein | 436/132 |
| 3,223,488 | 12/1965 | Luckey | 436/132 |
| 3,455,654 | 7/1969 | McConnaughey | 436/132 |
| 4,617,278 | 10/1986 | Reed | 436/60 |
| 4,791,065 | 12/1988 | Rislove | 436/132 |

Primary Examiner—James C. Housel
Assistant Examiner—N. Bhat

[57] ABSTRACT

Reagent is offered for the determining of the ethanol and method of determining the presence of ethanol in the human body by the method of processing of the biological material by the reagent, composed from the component 1, presenting itself as 0.06–0.36M of solution of sodium dichromate in water, and componet 2—concentrated sulphuric acid; during this biological material is added to the component 1, in the type of preferable saliva, soon after, component 2 is added with proportionate number of the components in volume 0.02–0.12:1:0.25–0.9. Mix and incubate in the period of 1.5–3 min. and determine the presence and quantity of the contained ethanol by the changing of the color carrier, saturated with liquid 3–10% solution of sodium nitroprissidi, 1–5% water solution of gelatine and 10–30% solution of morpholine in water, containing 1–20% multi-atom alcohol, under the effect of developing vapors, during the oxidation of the biological material. The color of the carrier changes during the presence of ethanol from light-grey to light-blue to dark blue, depending on the quantity of contained alcohol.

4 Claims, No Drawings

REAGENT FOR THE DETERMINATION OF ETHANOL AND METHOD OF DETERMINATION OF PRESENCE OF ETHANOL IN THE HUMAN BODY

The offered invention relates to the area of medicine, and particularly, to biochemistry, and intended for the determination of the presence of ethyl alcohol in the human body, and precisely: in its biofluids.

Known methods of determination of ethanol in the human body are based on the analysis of the exhaled air, blood, urine with the help of fermentative reactions, sensitive to the presence of alcohol, or chemical indicative systems on the base of such non-organic oxidizers Potassium permanganate and Potassium dichromate.

Among known chemical indicative test-systems, much greater use received the methods of determination of ethanol in the human body, which are based on the analysis of the exhaled air (tubes c,f Mohova-shinkarenko, "Control of soberness) and their foreign analogues [3]. Reagent of indicative tubes consists of carriers (silicagale), saturated with the solution of chrome anhydride in concentrated sulphuric acid. During the influence on the reagent of ethyl alcohol vapors, oxidizing, restoring reaction occurs, in the result of which changes the degree of chrome oxidation, that it leads to the change of colour of the reagent from orange or yellow to green. This colour change is valued as a positive reaction.

However, not considering the simplicity in methodical relation, this method possesses a series substantial deficiencies:

- significant quantity of false positive samples, not high enough sensitivity and accuracy of measurements;
- sensitivity to the presence in the exhaled air or in the surrounding atmosphere of the absorbed substances (acetone, benzine, exhaust gases, tobacco smoke and others in the air substances);
- large resistance of the filler of the tube to the insufflation of the exhaled air, that it makes it difficult to select the sample;
- the difficulty of the dosage of the exhaled air during the quantitative determination of the containing of the ethanol.

Besides that, this method of determination of containing of the ethanol, demands a well ventilated space, fully absent of any traces of smell of alcohol, Eau-de-cologne, ether, benzine, acetone, tobacco and others in the air substances from clothing, hands, observed people, that, obviously, only makes it more difficult to use this method in practice.

Much closer to the offered reagent and method in substance and to the achieved effect is the reagent for the determination of ethanol and method of determination of the presence of ethanol in the human body, concluding in that, that to the reagent 1, presenting itself 0.06–0.35M solution of Potassium dichromate and 0.03–0.4M of Potassium iodide in water, biological material is added, preferably saliva, following, reagent 2 is added-concentrated sulphuric acid, mix with the proportionate size of components in volume of reagent 1: biological material: reagent 2 0.02–0.12:1:0.25–0.9 is incubated in the period of 1.5–3 min. And with the changing of the colour and its intensiveness in comparison with the control the presence is determined and the quantity of the contained alcohol in the body (4; Kharchenko and others).

During the presence of ethanol in biological fluid and particularly in saliva, the colour of the reagent changes from light yellow-green to green-blue to dark-blue, depending on the quantity of the contained ethyl alcohol. Containment of the ethanol in the saliva is determined by comparison of the colour of the reagent with the colour scale.

However, not considering, that the well known prototype possesses great specificity, than the famous in the present time indicating substances, it is not specific enough to the series of drug preparations, such as validol, korvalol and others. Besides this, it changes colour under the influence of ethylenglycol, methanol, benzol and it's analogues. Besides that, the presence in the oral cavity of sugars, carbohydrates, can influence the colour change as well, that it will make the identification more difficult of the presence and determination of the dose of alcohol in the body, reduces accuracy and specificity of this method.

The aim of the offered invention is the increase of the specificity and accuracy of determination of the contained ethanol in the human body.

Taking into account, that the correlation of the containment of the ethanol in the blood and saliva composes 0.89–0.93% (by the data of the Ministry of Health care, U.S.S.R.) the set aim is achieved by the method of conducting the determination of ethanol in the human body by saliva, for the process of which the reagent is used, composed of the reagent 1, presenting itself 0.06–0.35M solution of sodium dichromate in water, and reagent 2 concentrated sulphuric acid; during this biological material is added to reagent 1, following reagent 2 is added in the proportionate size of components in volume 0.2–0.12:1:0.25–0.9, is mixed, incubated in the period 1.5–3 min. and determine the presence and quantity of the containing ethanol by the change of the colour carrier, saturated in water 3–10% sodium nitroprissidi, 1–5% water solution of gelatine and 10–30% solution of morpholine in water, containing 1–20% of multi-atom alcohol.

Substantial difference of the offered method from the prototype is the determination of the presence and quantity of the containing ethanol is conducted by the change of the colour carrier, for example paper, saturated with water 3–10% solution of sodium nitroprissidi, 1–5% water solution of gelatine and 10–30% solution of morpholine in water, containing 1–20% multi-atom alcohol, for example, ethyleneglycol or glycerine, under the influence of developing during the oxidation of biological material particularly saliva, vapors.

This difference, and also the use in the type of dichromate alkaline metal, sodium dichromate possessing in comparison with potassium dichromate substantially greater solubility in water and complicated multi component water solutions, allows to exclude from the composition of the reagent for the oxidation of the potassium iodide, necessary by the method-prototype for the previous oxidation of some metabolites, present in saliva, and increase the specificity and accuracy of determination.

The determination of the presence and quantity of containment of ethanol in the human body was conducted after 40 min.—1–2 hours after the intake by the person of the definite quantity of alcohol (in evaluation on pure ethyl alcohol); dose of alcohol in proml. was determined by the formula: dose in [0/00]=quantity of ethanol [in g]/weight of the person [in kg]; collection of saliva, taking of the blood and receiving of the serum was conducted by traditional methods. Condensate of the exhaled vapors was received by the method of insufflation of the exhaled air through the catcher, cooled by the ice.

EXAMPLE

In the test tube volume of 5 ml, 35 microliters of water solution was placed, containing 1.75 mg of sodium, dichromate (reagent 1 presenting itself 0.19M solution of sodium dichromate in water), following, add 700 microliters of saliva, collected from the observed person after 2 hours after the intake of 75 g of pure ethyl alcohol/weight of the person 75 kg: Definite dose of alcohol composed 1.0 0/00/ and 400 microliters of the concentrated sulphuric acid (reagent 2)/proportionate size of the reagent 1: biological material: reagent 2 0.05 1:0.61; is mixed and incubated in the period of 2 min. Colour change is observed of the filter paper, saturated with 5% of sodium nitroprissidi solution, 3% solution of gelatin and 15% solution of morpholine in water, containing 10% of glycerin, from light-grey to blue, that it corresponds to the dose of 0.85-1.15 0/00.

Examples 2-9 are also conducted as example 1, conditions of conducting the determination of ethanol and received results presented in Table 1.

Examples 10 and 11 are also conducted as example 1, but in the type of biological material, serum of the blood is used (example 10) or condensate of exhaled vapors (example 11).

Examples 12-17 are conducted as example 1, changing only the conditions of the saturation of the carrier. Received results are presented in Table 2.

During the use of proportional sizes of reagent 1: biological material: reagent 2 more than 0.12:1:0.9 and less than 0.02:1:0.25; and also during the use of sodium dichromate solution more than 0.35M and less than 0.06M accuracy of the determination of the presence and quantity of the contained alcohol significantly decreases.

The use for the saturation of the carrier of the solution reagents over the limits of the claimed concentrations also decreases the accuracy of the determination.

In the Table 3, comparative characteristics are shown of the specificity of the enclosed method in comparison with the method-prototype. Testing was conducted by the method of introduction in the collected saliva of the observed person of the researched chemical substances.

As evident from the presented Table 3, the offered method possesses greater, specificity, than method-prototype, since it does not change its colour under the influence of such substances as ethylenglycol, benzol, sugar, and also drug preparations: validol, korvalol.

This way, the offered reagent and method of determination of presence of alcohol in the human body in comparison with method-prototype allows to increase the specificity and accuracy of the determination of ethanol because of the decrease of false positive samples on the series of combinations, interfering with the determination during the use of method-prototype.

TABLE 1

Determination of the presence and quantity of the containment of ethanol in the human body

| No. | Evaluated dose of Ethanol 0/00 | Biological Material | Reagent 1 Quantity micro/ liters | Reagent 1 Concentration Sodium Dichromate | Proportionate size of Reagent 1 in volume: Reagent 2 | Time of incubation, minutes | Colour of the carrier | Definite Dose of Ethanol 0/00 |
|---|---|---|---|---|---|---|---|---|
| 1 | 2 | 3 | 4 | 5 | 6 | 7 | 8 | 9 |
| 1 | 1.0 | saliva | 35 | 0.19M | 0.05:1:0.6 | 2 | light-blue | 0.85-1.15 |
| 2 | " | " | 60 | 0.06M | 0.12:1:0.25 | 3 | " | " |
| 3 | " | " | 40 | 0.35M | 0.02:1:0.9 | 1.5 | " | " |
| 4 | 0 | " | 35 | 0.2M | 0.1:1:0.7 | 2 | light-light grey | 0 |
| 5 | 0.4 | " | " | " | " | " | light-light blue | 0.3-0.6 |
| 6 | 1.5 | " | " | " | " | " | dark-blue | 1.35-1.65 |
| 7 | 2.0 | " | " | " | " | " | light-blue | 1.85-2.15 |
| 8 | 2.5 | " | " | " | " | " | blue | 2.35-2.65 |
| 9 | 3.0 | " | " | " | " | " | dark-blue | 2.85-3.15 |
| 10 | 1.0 | serum of blood | 50 | 0.19M | 0.05:1:0.6 | " | light | 0.85-1.15 |
| 11 | 1.0 | condensate | " | " | " | " | light blue | 0.85-1.15 |

TABLE 2

Affirmation of the declared concentration intervals of the reagents, used for the saturation of the carriers.

| Number of Carrier | | Concentration, % | | | | Colour of the Carrier | Definite dose of Ethanol, 0/00 |
|---|---|---|---|---|---|---|---|
| | | Sodium Nitro-Prissidi | Gelatin | Morpholine | Multi-Atom Alcohol | | |
| 12 | paper | 5 | 3 | 12 | glycerin 15 | light-blue | 0.85-1.15 |
| 13 | " | 3 | 1 | 10 | glycerin.20 | " | " |
| 14 | " | 10 | 5 | 20 | glycerin,1 | " | " |
| 15 | cotton | 4 | 4 | 17 | ethylen-glycol,14 | " | " |
| 16 | cotton | 2 | 0.8 | 9 | ethylen-glycol,0.7 | grey | determination impossible |
| 17 | paper | 12 | 7 | 35 | glycerin | black | determination |

TABLE 2-continued

Affirmation of the declared concentration intervals of the reagents, used for the saturation of the carriers.

| Number of Carrier | Concentration, % | | | | Colour of the Carrier | Definite dose of Ethanol, 0/00 |
|---|---|---|---|---|---|---|
| | Sodium Nitro-Prissidi | Gelatin | Morpholine | Multi-Atom Alcohol | | |
| | | | | 23 | | impossible |

TABLE 3

Comparative characteristics of specificity of the offered method and prototype

| Research Factor (chemical substance) | Change of Colour under the influence of the Research Factor | |
|---|---|---|
| | Prototype | Offered Method |
| Colour of the Reagent | light yellow-green | light-grey |
| Ethyl Alcohol | green, blue | light blue, blue |
| Methyl Alcohol | green, blue | light-grey |
| Acetone | light yellow-green | red |
| Ether Glutar | " | light-grey |
| Athydride | " | " |
| Chloroform | " | " |
| Benzine | " | " |
| Benzol | orange-brown | " |
| Alkaline (NaOM) | light yellow-green | " |
| Ethylene Glycol | blue-green | " |
| Validol | blue-green | " |
| Korvalol | blue-green | " |
| sugar | blue-green | " |
| pyrdine | light yellow-green | " |
| phenol | " | " |
| Dichloride | " | " |

The invention relates to the area of medicine, particularly to biochemistry, and is intended for the determination of the presence ethyl alcohol in the human body, expecially in the biological fluids.

The aim of the invention—increase the accuracy of the method.

Method is realized as follows.

Reagent is used, which is composed of the reagent 1, presenting itself in 0.06–0.35M solution of sodium dichromate in water, and reagent 2—concentrated sulphuric acid. To the reagent 1, biological material is added, following, reagent 2 is added in the proportionl size of components in volume 0.2–0.12:1:0.25–0.9 is mixed, incubated in the period 1.5–3 min and determine the presence and quantity of contained ethanol by the change of the colour carrier (for example, paper ), saturated in water 3–10% solution of sodium nitroprissidi, 1–5% of water solution of gelatine and 10–30% solution of morpholine in water, containing 1–20% of multi-atom alcohol, for example ethyleneglycol and glycerine.

Method is described with the following examples.

Determination of presence and quantity of the containment of ethanol in the human body was conducted after 40 min to 1-2 hours after the intake by the person of a definite quantity of alcohol (in evaluation on pure ethylalcohol); dose of alcohol in promil. was determined by the formula: dose in (0/100)=quantity of ethanol (in g)/weight of the person (in kg); collection of saliva, taking of the blood and receiving of the serum was conducted by the traditional methods. Condensate of the exhaled vapors was received by the method of insufflation of the exhaled air throuh the catcher, which is cooled by ice.

Example 1

In the test tube, size of 5 ml, place 35 microliters of water solution, containing 1.75 mg of sodium dichromate (reagent 1, presenting itself in 0.19M of solution of sodium dichromate in water), following add 70 microliters of saliva, collected from the observed person after 2 hours after the intake of 75 g of pure ethyl alcohol (weight of the person 75 kg, estimated dose of alcohol composes 1.0 0/100) and 400 microliters of the concentrated sulphuric acid reagent 2) (proportionate size of reagent 1 in volume: biological material: reagent 2 0.05:1:0.6) is mixed and incubated in the period of 2 min. Changes are observed of the colour of the filter paper, saturated with 5% solution of sodium nitroprissidi, 3% solution of gelatine and 15% solution of morpholine in water, containing 10% of glycerine, from light-grey to blue, that corresponds to the dose 0.85–1.15 0/00.

Examples 2–9 are also conducted as example 1, conditions of conducting the determination of ethanol and the received results are presented in table 1.

TABLE 1

Determination of the presence and quantity of the contained ethanol in the human body.

| No. | Estimated dose of ethanol, 0/00 | Biological Material | Reagent 1 | | Proportionate size in volume of reagent 1; biological material: Reagent 2 | Time of incubation in min. | Colour of the carrier | Definite dose of ethanol 0/00 |
|---|---|---|---|---|---|---|---|---|
| | | | Quantity, microliters | Concentration of sodium dichromate | | | | |
| 1 | 1.0 | saliva | 35 | 0.19M | 0.05:1:0.6 | 2 | light blue | 0.85–1.5 |
| 2 | " | " | 60 | 0.06M | 0.12:1:0.25 | 3 | " | " |
| 3 | " | " | 40 | 0.35M | 0.02:1:0.9 | 1.5 | " | " |
| 4 | 0 | " | 35 | 0.2M | 0.1:1:0.7 | 2 | light grey | 0 |
| 5 | 0.4 | " | " | " | " | " | light–light blue | 0.3–0.6 |
| 6 | 1.5 | " | " | " | " | " | dark–light blue | 1.35–1.65 |
| 7 | 2.0 | " | " | " | " | " | light blue | 1.85–2.15 |
| 8 | 2.5 | " | " | " | " | " | blue | 2.35–2.65 |
| 9 | 3.0 | " | " | " | " | " | dark | 2.85–3.15 |
| 10 | 1.0 | blood serum | 50 | 0.19M | 0.05:1:0.6 | " | light blue | 0.85–1.15 |

TABLE 1-continued

Determination of the presence and quantity of the contained ethanol in the human body.

| No. | Estimated dose of ethanol, 0/00 | Biological Material | Reagent 1 Quantity, microliters | Reagent 1 Concentration of sodium dichromate | Proportionate size in volume of reagent 1; biological material: Reagent 2 | Time of incubation in min. | Colour of the carrier | Definite dose of ethanol 0/00 |
|---|---|---|---|---|---|---|---|---|
| 11 | 1.0 | condensate | " | " | " | " | light blue | 0.85–1.15 |

TABLE 2

Confirmation of the declared concentrated intervals of the reagents, used for the saturation of the carrier

| No. | Carrier | Concentration % Sodium Nitro prissidi | Gelatine | Morpholine | Multi-Atom Alcohol | Colour of Carrier | Definite dose of Ethanol, 0/00 |
|---|---|---|---|---|---|---|---|
| 12 | paper | 5 | 3 | 12 | glycerine 15 | light blue | 0.35–1.15 |
| 13 | " | 3 | 1 | 10 | glycerine,20 | " | " |
| 14 | " | 10 | 5 | 30 | glycerine,I | " | " |
| 15 | cotton | 4 | 4 | 17 | ethylene glycol, 14 | " | " |

TABLE 3

Comparative characteristics of the specificity of offered method and prototype

| Research Factor (chemical substance) 1 | Change of colour under the influence of the research factor Prototype 2 | Change of colour under the influence of the research factor Offered Method 3 |
|---|---|---|
| colour of the reagent | light yellow-green | light grey |
| ethyl alcohol | green, blue | light blue, blue |
| methyl alcohol | green, blue | light grey |
| Acetone | light yellow-green | red |
| Ether | " | light grey |
| Glutar Aldegride | " | " |
| Chloroform | " | " |
| Benzin | " | " |
| Benzol | orange-brown | light-grey |
| alkaline (NaOH) | light yellow-green | " |
| Ethyleneglycol | blue-green | " |
| Validol | blue-green | " |
| Korvalol | blue-green | " |
| Sugar | blue-green | " |
| Pyridine | light yellow-green | " |
| Phenol | " | " |
| Dichlorethan | " | " |

As evident from the presented Table 3, the offered method possesses a greater specificity, than method-prototype, since it does not change it's colour under the influence of such substances as ethyleneglycol, benzol, sugar, and also drug preparations; validol, korvalol.

By this means, the offered reagent and method of determination of the presence of alcohol in the human body, in comparison with the method-prototype, allows to increase the specificity and accuracy of the determination of ethanol because of the decreasing false positive samples on the series of combinations, interfering with the determination during the use of method-prototype.

What is claimed is:

1. A method for determining the concentration of ethanol in biological fluids, comprising:

mixing an aqueous solution of sodium dichromate and concentrated sulphuric acid with an effective amount of biological fluid;

impregnating a carrier with an aqueous solution of nitroprusside and gelatine and an aqueous solution of morpholine and glycerine; exposing said impregnated carrier to vapours produced when said aqueous solution of sodium dichromate and concentrated sulphuric acid is mixed with said biological fluid whereby at least a portion of said carrier changes colour to indicate the concentration of ethanol in said biological fluid.

2. A method for determining the concentration of ethanol in saliva, comprising:

mixing an aqueous solution of sodium dichromate and concentrated sulphuric acid with an effective amount of saliva;

impregnating a carrier with an aqueous solution of nitroprusside and gelatine and locally saturating same with an aqueous solution of morpholine and glycerine;

exposing said carrier to vapours produced when said aqueous solution of sodium dichromate and concentrated sulphuric acid is mixed with said saliva.

3. A method for determining the concentration of ethanol in saliva according to claim 2 wherein said impregnating and locally saturating step comprises impregnating a carrier with a 3 to 10% aqueous solution of nitroprusside and a 1 to 5% aqueous solution of gelatine and locally saturating said carrier with a 10 to 30% aqueous solution of morpholine containing 1 to 20% of glycerine.

4. A method for determining the concentration of ethanol in saliva according to claim 3 wherein said mixing step comprises mixing 0.2 to 0.12 parts of a 0.06 to 0.35M aqueous solution of sodium dichromate with one part of saliva and with 0.25 to 0.9 parts of concentrated sulphuric acid.

* * * * *

UNITED STATES PATENT AND TRADEMARK OFFICE
CERTIFICATE OF CORRECTION

PATENT NO. : 5,403,749
DATED : April 4, 1995
INVENTOR(S) : Serguei V. KHARTCHENKO, Kiril E. GIATSINTOV, Andrei V. ALEKSANDROV and Nadejda P. KHARTCHENKO It is certified that error appears in the above-indentified patent and that said Letters Patent is hereby corrected as shown below:

On the cover page, under [75] Inventors, "Kiril Giatsintov" should read --Kiril E. Giatsintov--.

Signed and Sealed this

Twenty-seventh Day of June, 1995

*Attest:*

BRUCE LEHMAN

*Attesting Officer*   *Commissioner of Patents and Trademarks*